(12) United States Patent
Pryor

(10) Patent No.: US 11,648,146 B2
(45) Date of Patent: May 16, 2023

(54) LOW PROFILE BEDPAN

(71) Applicant: Monya Faye Pryor, Hendersonville, TN (US)

(72) Inventor: Monya Faye Pryor, Hendersonville, TN (US)

( * ) Notice: Subject to any disclaimer, the term of this patent is extended or adjusted under 35 U.S.C. 154(b) by 0 days.

(21) Appl. No.: 15/082,030

(22) Filed: Mar. 28, 2016

(65) Prior Publication Data
US 2017/0273818 A1 Sep. 28, 2017

(51) Int. Cl.
*A61F 5/455* (2006.01)
*A47K 11/12* (2006.01)
*A61G 9/00* (2006.01)

(52) U.S. Cl.
CPC ............ *A61F 5/4556* (2013.01); *A47K 11/12* (2013.01); *A61G 9/006* (2013.01)

(58) Field of Classification Search
CPC ........ A47K 11/06; A47K 11/12; A47K 13/08; A61F 5/4556; A61G 9/00; A61G 9/003; A61G 9/006
USPC ..................... 4/144.1, 144.2–144.4, 450–548
See application file for complete search history.

(56) References Cited

U.S. PATENT DOCUMENTS

| | | | | |
|---|---|---|---|---|
| 381,972 A | * | 5/1888 | Tooker | A61G 9/003 4/450 |
| 1,340,680 A | * | 5/1920 | Zimmerman | A61G 9/003 4/450 |
| 1,657,975 A | * | 1/1928 | Shiells | A61G 9/006 4/144.1 |
| 1,928,170 A | * | 9/1933 | Dwork | A61F 5/455 4/144.4 |
| 2,182,254 A | * | 12/1939 | Farrell | A61F 5/455 4/144.3 |
| 2,195,156 A | * | 3/1940 | Steward | A61G 9/003 4/455 |
| 2,358,850 A | * | 9/1944 | Chenault | A61G 9/006 222/538 |
| 2,359,830 A | * | 10/1944 | Deckert | A61G 9/003 5/604 |
| 2,491,799 A | * | 12/1949 | Ella | A61F 5/451 4/144.2 |
| 2,711,543 A | * | 6/1955 | Steward | A61G 9/003 4/455 |
| 3,095,578 A | * | 7/1963 | Stanford | A61F 5/44 248/99 |
| 3,444,563 A | * | 5/1969 | Gordon, Jr. | A47K 11/04 4/484 |
| 3,992,729 A | * | 11/1976 | Mills | A61G 9/003 4/450 |
| 4,531,245 A | * | 7/1985 | Lowd | A47K 11/00 141/337 |
| 4,771,484 A | * | 9/1988 | Mozell | A61F 5/4556 4/144.4 |

(Continued)

*Primary Examiner* — Erin Deery
(74) *Attorney, Agent, or Firm* — Bradley Arant Boult Cummings LLP; Timothy L. Capria; Alexandra C Lynn

(57) ABSTRACT

A device for capturing and disposing of urine comprises an elongated body. The elongated body includes a top surface, a handle end, and a neck end opposite of the handle end. The device comprises an open neck extending in a direction away from the top surface. The device comprises a groove disposed substantially along the top surface toward the open neck, the groove including a groove wall that extends downwardly from the handle end to the neck end. A bag may be removably disposed on the open neck.

20 Claims, 4 Drawing Sheets

(56) References Cited

U.S. PATENT DOCUMENTS

| | | | | |
|---|---|---|---|---|
| 5,331,689 | A * | 7/1994 | Haq | A47K 11/12 |
| | | | | 4/144.1 |
| D370,975 | S * | 6/1996 | Mohr | 4/144.1 |
| 5,819,334 | A * | 10/1998 | Maze | A61G 9/003 |
| | | | | 4/450 |
| 5,920,916 | A * | 7/1999 | Norton | A61B 10/007 |
| | | | | 4/144.3 |
| D467,338 | S * | 12/2002 | Rehrig | D24/122 |
| 6,532,604 | B2 * | 3/2003 | Moser | A61G 9/003 |
| | | | | 4/450 |
| 6,651,259 | B1 * | 11/2003 | Hartman | A61B 10/007 |
| | | | | 4/144.1 |
| D607,995 | S * | 1/2010 | Miller | D24/122 |
| 2002/0193762 | A1 * | 12/2002 | Suydam | A61F 5/4556 |
| | | | | 604/327 |
| 2015/0305917 | A1 * | 10/2015 | Su | A61F 5/451 |
| | | | | 4/144.1 |
| 2016/0128524 | A1 * | 5/2016 | Poore | A47K 11/12 |
| | | | | 4/144.1 |

* cited by examiner

LOW PROFILE BEDPAN

BACKGROUND OF INVENTION

Females who are not able to walk to the bathroom, or transfer from a bed or a wheelchair to a toilet or bedside commode, traditionally have used bedpans. However, it is difficult for females having compromised mobility to urinate while positioned on their backs, especially as females have spent most of their life urinating in a seated position. Moreover, traditional bedpans are disadvantageous, as they must be positioned perfectly to reduce spillage of urine. This has resulted in many women who are unable to walk or transfer to a bedside commode or toilet to decrease their fluid intake, as they desire to avoid frequent urination. Thus, a need exists for a more convenient and comfortable devices to assist subjects in urination.

BRIEF SUMMARY

The disclosed devices and methods are related to a female urinal for hands free use that reduces spillage of urine. The device assists females with urination who are unable to walk safely to and from the bathroom, who are unable to transfer from bed to a commode chair, or who require immediate release of urine in a seated position. The device can be used with the assistance of another person, which is beneficial should the user be physically disabled or have hand impairments.

DETAILED DESCRIPTION

Figure 1:
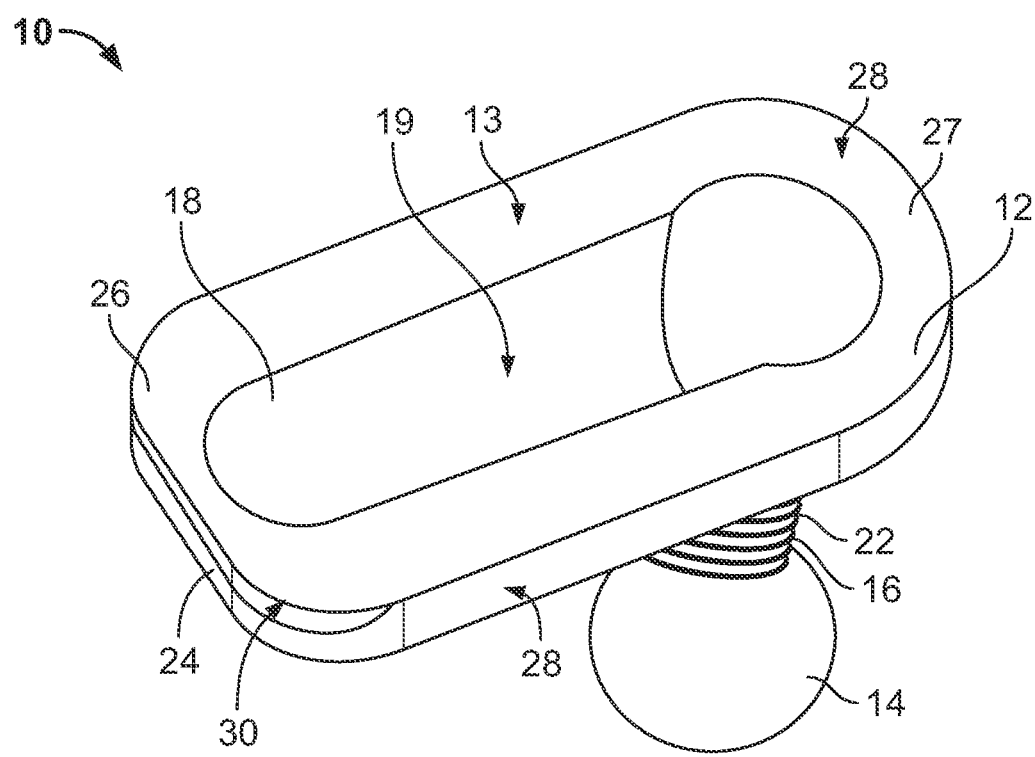
FIG. 1 illustrates a top perspective view of an embodiment of the device.

A device 10 for sequestering urine has been developed. The device 10 reduces the need for a bedpan for urination if the user (e.g., a patient) is able to sit in an upright position, such as at a bedside. Indeed, the device 10 can be used in a wheel chair, a car seat, or wherever a user can sit in an upright position. Beneficially, the device 10 reduces the need of the user to transfer from a wheelchair to a commode or a toilet to urinate, allowing women who have limited mobility the ability to use public restrooms and use the device 10 without needing for assistance with transferring onto a commode or toilet for urination.

The device 10 comprises an elongated body 12 including a top surface 13 and a bottom external surface 29 opposite of the top surface 13. The device 10 may comprise a removable bag 14 (e.g., an ice bag) to hold urine. The body 12 and the bag 14 can be joined by, for example, cooperative threading 16 such that the body 12 and the bag 14 may be coupled and uncoupled by twisting the body 10 and the bag 14 relative to one another. The bag 14 may be constructed of a polymer and may be flexible, such as when constructed from latex. The bag 14 may have an interior volume of, for example, 64 fluid ounces. Advantageously, the bag 14 hides and assists in disposing of captured urine.

The device 10 may be constructed of a polymer. One or more external surfaces 28 (e.g., the top surface 13 and the bottom external surface 29) of the device 10 may be smooth. The device 10 includes a handle end 26 and a neck end 27 that is opposite of (i.e., on the other longitudinal side of) the device 10 from the handle end 26. The handle end 26 may have a curved profile (e.g., a bill, or visor). A handle 24 may be disposed at the handle end 26 of the device.

The device 10 includes an open neck 22 disposed in the bottom external surface 29 at the neck end 27 of the device 10. The bag 14 may be coupled and uncoupled from the body 12 via the open neck 22. For example, the bag 14 may be removed (e.g., twisted off) from the open neck 22, such as for emptying or replacement of the bag 14.

Figure 2:
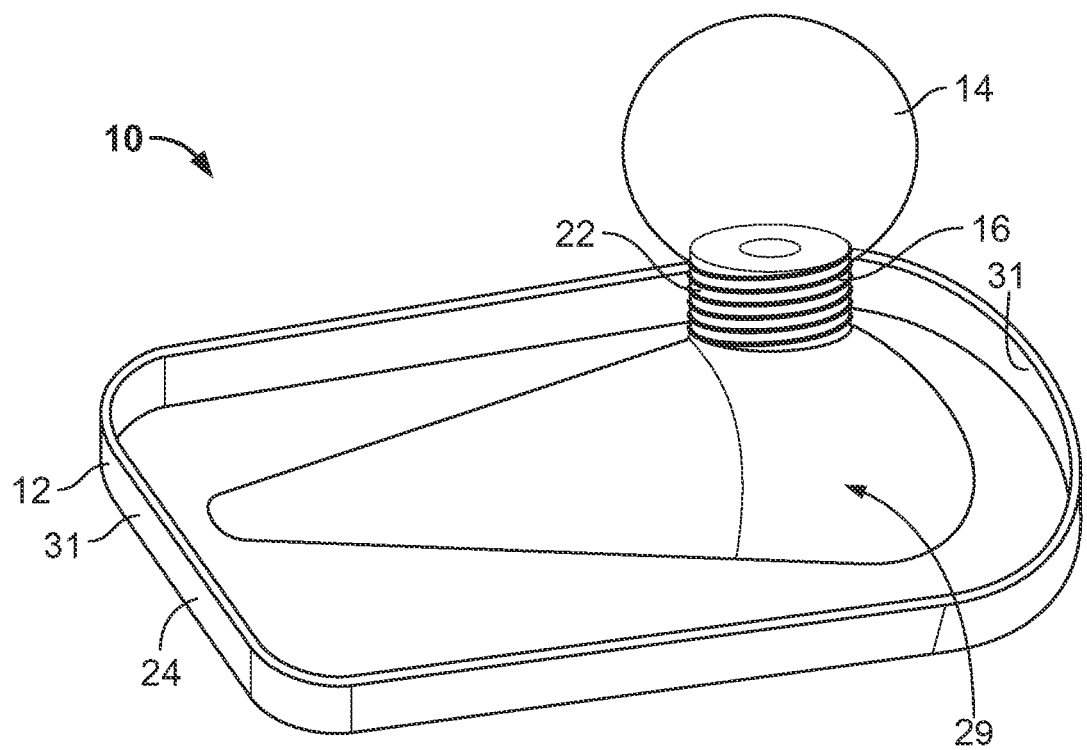
FIG. 2 illustrates a bottom perspective view of the embodiment of FIG. 1.

A groove 18 may be formed in the top surface 13 of the device. The groove 18 is in fluid communication with the open neck 22, such that any fluids (e.g., urine) that enter the groove 18 can pass through the open neck 22 and, subsequently, into the bag 14. The groove 18 may begin a distance 32 (such as one inch) from the handle end 26 and extend across the top surface 13 of the device and terminate a distance (such as one inch) from the neck end 27. The groove 18 may include a groove wall 19 that extends downwards from the top surface 13. The groove wall 19 may define a slope relative to the top surface 13. For example, the groove 18 may slope downwardly from the top surface 13 to the open neck 22 of the bottom external surface 29, as the groove 18 extends from the handle end 26 to the neck end 27 (e.g., see FIGS. 1, 2, and 7). That is, the depth of the groove 18 may be shallower at the handle end 26 of the device 10 as compared to the groove's depth at the neck end 27 of the device 10. The downward slope directs urine to flow down the groove 18, through the open neck 22, and into the bag 14.

Figure 5:
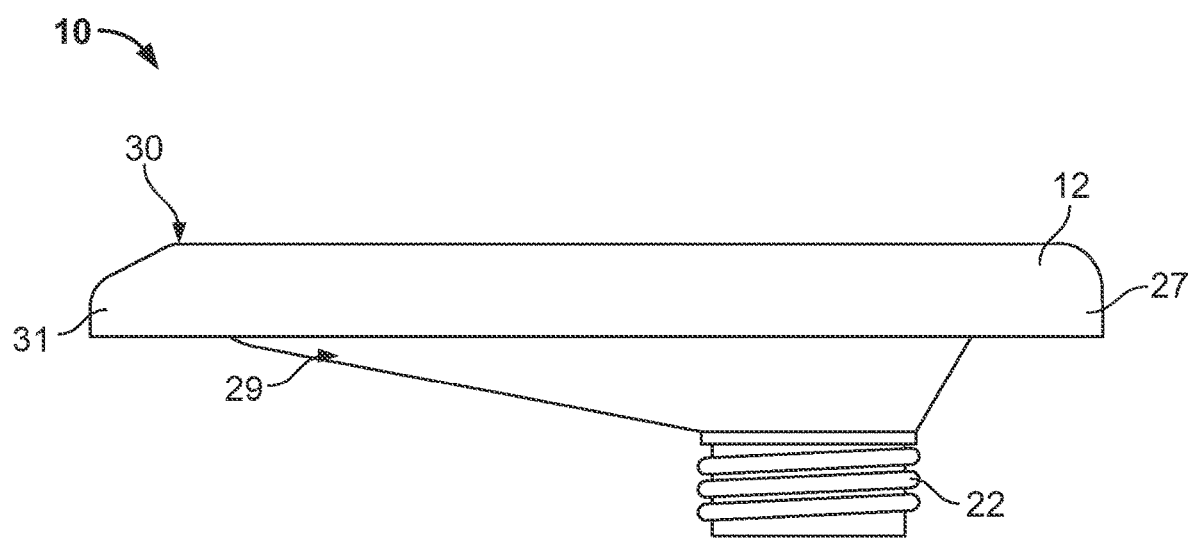
FIG. 5 illustrates a side view according to the embodiment of the device shown in FIG. 4.
Figure 6:
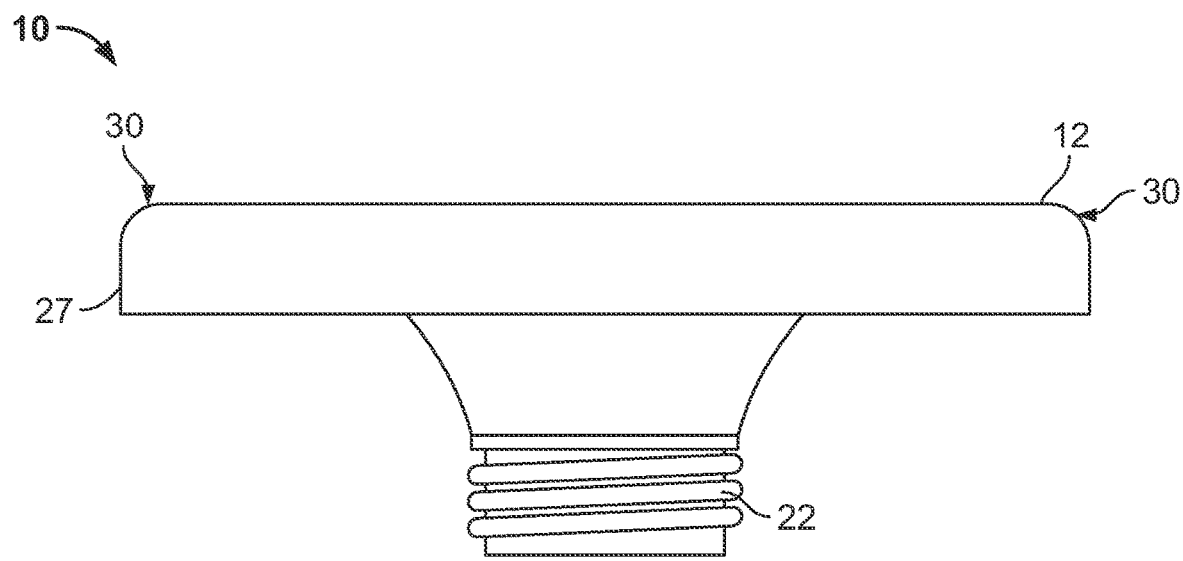
FIG. 6 illustrates a rear view according to the embodiment of the device shown in FIG. 4.

The groove 18 may define the bottom external surface 29 of the device 10. In said embodiment, the bottom external surface 29 likewise slopes downward towards the open neck 22, as the bottom external surface 29 extends from the handle end 26 to the neck end 27 of the device. This embodiment is illustrated, for example, in FIGS. 2, 5, and 7, wherein the sloped shape of the groove 18 defines the sloped shape of the bottom external surface 29 of the device 10.

Figure 3:
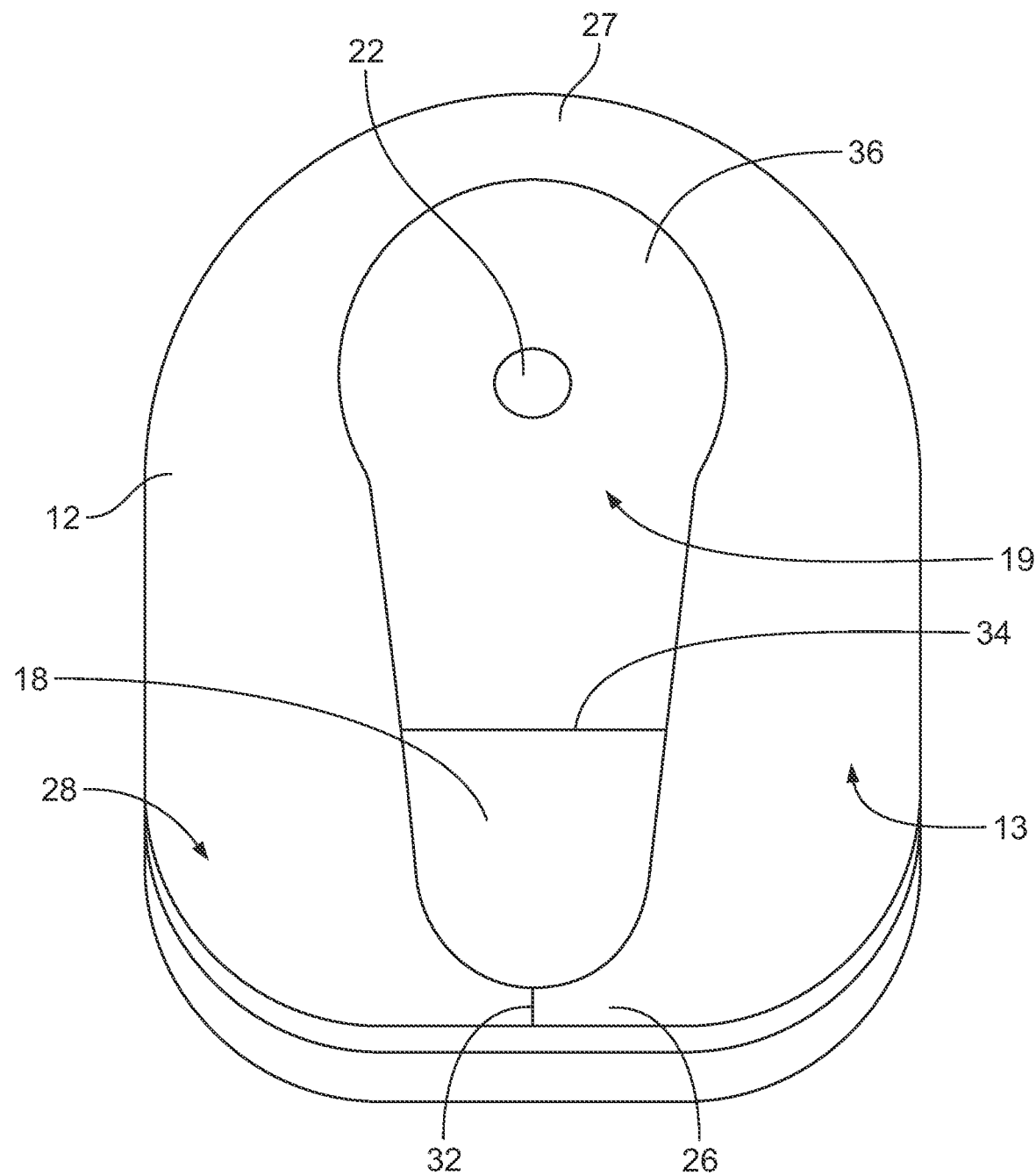
FIG. 3 illustrates a top perspective view according to an embodiment of the device.
Figure 4:
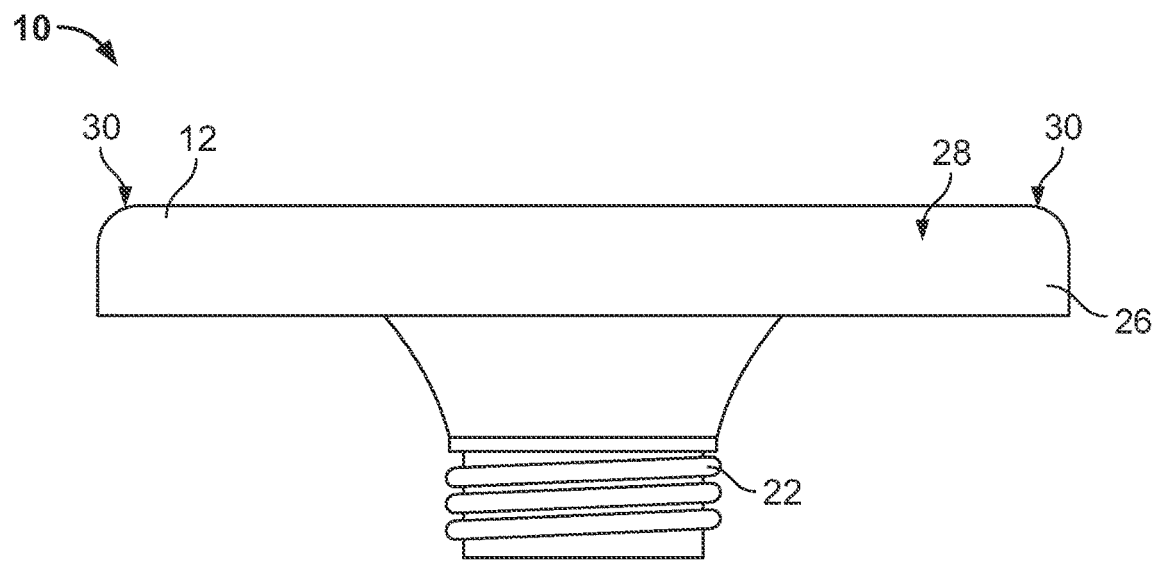
FIG. 4 illustrates a front view according to an embodiment of the device.

The device 10 may have a width of approximately 6 inches and a length of approximate 9 to 9.5 inches from the handle end 26 to the neck end 27. The elongated body 12 of the device 10 may have a height 33 of approximately 2.5 inches, as measured from the top surface 13 to the open neck 22 of the bottom external surface 29 (see FIG. 7). The groove 18 may have a groove width 34 of approximately 2 inches (see FIG. 3). The groove 18 may have a groove base 36, or cavity 36, which may have a circular, or hemispherical, profile that curves inwardly toward the open neck 22 and into the bag 14. Advantageously, this profile reduces the spillage of urine in the device 10.

As shown in FIGS. 4-7, the top surface 13 of the device 10 may have one or more edges 30. The one or more edges 30 may be circumferentially disposed around the top surface 13. A lip 31 may extend downwards from the one or more edges 30 of the top surface 13 (see, e.g., FIGS. 2, 5, and 7). That is, the one or more edges 30 form a junction between the top surface 13 and the lip 31. The lip 31 may be disposed around, and extend downwards from, the entire circumference of the top surface 13. Conveniently, the lip 31 may function as the handle 24.

Figure 7:
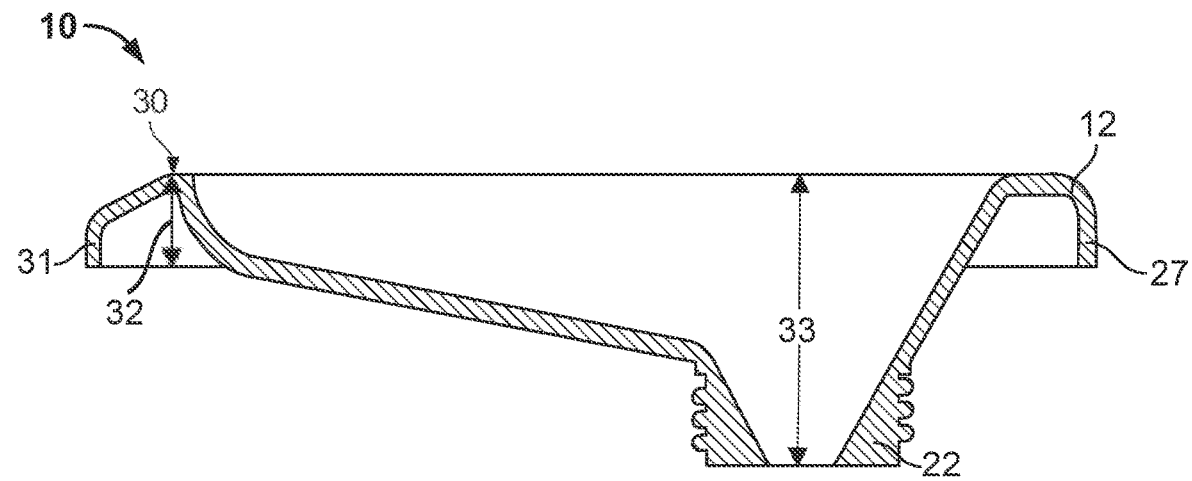
FIG. 7 illustrates a cross sectional side view according to the embodiment of the device shown in FIG. 4.

The lip may have a lip height 32 of approximately ⅝ inch to ¾ inch, as measured vertically from the one or more edges 30 from which the lip extends to a bottom of the lip (see FIG. 7). The lip height 32 may be shorter than the elongated body height 33, such that the lip is not flush with the bottom external surface 29 (see FIGS. 5 and 7). For instance, the lip height 32 may be less than one third of the elongated body height 33.

The device 10 may be used by a person, or user, positioned in a seated or semi-reclined position. The device 10 may be slid, or positioned, between legs (i.e., thighs) of the user such that the groove 18 is positioned directly underneath the urethra of the user. The user may position her legs in an abducted (i.e., spread) position to use the device 10. The placement of the device 10 may be visually verified by the user to ensure the device 10 is positioned correctly. The user may urinate into the groove 18. The urine will flow along the slope of the groove (i.e., away from the handle end 26 and towards the neck end 27) and through the open neck 22 and into the bag 14. The bag 14 may be removed (e.g., twisted off) from the open neck 22 and emptied of the sequestered urine. The device 10 may be repositioned, or removed from under the user, by the handle 24 disposed at the handle end 26 of the device. The device 10 may be cleaned with a disinfectant and reused.

Thus, although there have been described particular embodiments of the present invention of a new and useful device and methods for sequestering urine, it is not intended that such references be construed as limitations upon the scope of this invention except as set forth in the following claims.

What is claimed is:

1. A device for capturing and disposing of urine from a subject positioned in a reclined, semi-reclined, or seated position on a furniture surface, comprising:
   an elongated body including:
      an elongated body height,
      a top surface,
      a bottom external surface opposite on the body from the top surface, the bottom external surface including an open neck extending in a direction away from the top surface,
      a groove extending from the top surface and towards the open neck, the groove defining the bottom external surface,
      a lip circumferentially disposed around the groove and extending downwardly from the top surface, wherein the lip is not flush with the bottom external surface and extends no more than a third of the elongated body height,
      a neck end proximate to the open neck, and
      a handle end opposite on the body from the neck end, the handle end including a handle defined by the lip,
   wherein the groove continuously widens and slopes downwardly from the top surface to the open neck of the bottom external surface as the groove extends from the handle end to the neck end such that the bottom external surface slopes continuously downward toward the open neck, and
   wherein the device is shaped to slide between and under legs of the subject and between the subject and the furniture surface so that the groove is positioned between the subject and the furniture surface.

2. The device of claim 1, wherein the open neck comprises external threading.
3. The device of claim 1, further comprising a bag removably disposed on the open neck.
4. The device of claim 1, further comprising a cavity disposed at the neck end of the groove.
5. The device of claim 4, wherein the cavity has a rounded profile.
6. The device of claim 4, wherein the cavity is in fluid communication with the open neck.
7. The device of claim 1, wherein the body is integrally formed.
8. The device of claim 1, wherein the body is constructed of a polymer.
9. The device of claim 1, wherein the lip is rounded in profile at the handle end.
10. The device of claim 1, wherein the lip has a height of from ⅝ inch to ¾ inch.
11. The device of claim 1, wherein the body comprises an equal width across the top surface along the groove.
12. A method of sequestering urine from a subject positioned in a reclined, semi-reclined, or seated position on a furniture surface, comprising:
    providing a device comprising:
       an elongated body including:
          an elongated body height,
          a top surface,
          a bottom external surface opposite on the body from the top surface, the bottom external surface including an open neck extending in a direction away from the top surface,
          a groove extending from the top surface and towards the open neck, the groove defining the bottom external surface,
          a lip circumferentially disposed around the groove and extending downwardly away from the top surface, wherein the lip is not flush with the bottom external surface and extends no more than a third of the elongated body height,
          a neck end proximate to the open neck, and
          a handle end opposite on the body from the neck end, the handle end including a handle defined by the lip,
       wherein the groove continuously widens and slopes downwardly from the top surface to the open neck of the bottom external surface as the groove extends from the handle end towards the neck end such that the bottom external surface slopes continuously downward toward the open neck;
    sliding the device between and under legs of the subject and between the subject and the furniture surface;
    positioning the groove underneath a urethra of the subject; and
    when the subject urinates, sequestering urine that flows along the groove from the handle end to the neck end.
13. The method of claim 12, wherein the device includes a bag removably disposed on the open neck.
14. The method of claim 13, wherein the urine is sequestered into the bag.
15. The method of claim 14, further comprising removing the bag after urine is sequestered.
16. The method of claim 12, wherein thighs of the subject are in an abducted position.
17. The method of claim 12, wherein the body is integrally formed.
18. The method of claim 12, wherein the lip of the device is rounded in profile at the handle end.

19. The method of claim 12, wherein the lip of the device has a height of from ⅝ inch to ¾ inch.

20. The method of claim 12, wherein the body of the device comprises an equal width across the top surface along the groove.

\* \* \* \* \*